United States Patent
Batzer (10) Patent No.: US 10,244,292 B2
(45) Date of Patent: *Mar. 26, 2019

(54) METHOD AND DEVICE FOR DETECTING BIOELECTRIC SIGNALS

(71) Applicant: Siemems Healthcare GmbH, Erlangen (DE)

(72) Inventor: Ulrich Batzer, Buckenhof (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 42 days.

This patent is subject to a terminal disclaimer.

(21) Appl. No.: 15/283,402

(22) Filed: Oct. 1, 2016

(65) Prior Publication Data

US 2017/0099528 A1   Apr. 6, 2017

(30) Foreign Application Priority Data

Oct. 1, 2015   (DE) .......................... 10 2015 219 037

(51) Int. Cl.
| | |
|---|---|
| *A61B 17/32* | (2006.01) |
| *H04Q 9/00* | (2006.01) |
| *A61B 5/0402* | (2006.01) |
| *A61B 5/00* | (2006.01) |
| *A61B 5/0428* | (2006.01) |

(52) U.S. Cl.
CPC ............. *H04Q 9/00* (2013.01); *A61B 5/0402* (2013.01); *A61B 5/0428* (2013.01); *A61B 5/7203* (2013.01); *A61B 5/7225* (2013.01); *H04Q 2209/86* (2013.01)

(58) Field of Classification Search
CPC ... A61B 5/0402; A61B 5/0428; A61B 5/7203; A61B 5/7225
See application file for complete search history.

(56) References Cited

U.S. PATENT DOCUMENTS

| | | | |
|---|---|---|---|
| 6,306,100 B1 * | 10/2001 | Prass ................... | A61B 5/0488 128/908 |
| 9,717,431 B2 * | 8/2017 | Batzer ................. | A61B 5/0408 |
| 2016/0095528 A1 | 4/2016 | Batzer et al. | |

FOREIGN PATENT DOCUMENTS

DE   102014219943 A1   4/2016

OTHER PUBLICATIONS

German office Action for related German Application No. 10 2015 219 037.4 dated Jun. 3, 2016, with English Translation.

* cited by examiner

*Primary Examiner* — Alyssa M Alter
(74) *Attorney, Agent, or Firm* — Lempia Summerfield Katz LLC (57) ABSTRACT

A method for operating a bioelectric differential measurement arrangement includes detecting a bioelectric measurement signal. The bioelectric measurement signal includes a bioelectric useful signal and an interference signal. The method also includes detecting the interference signal by a common-mode current measurement by the bioelectric differential measurement arrangement.

9 Claims, 5 Drawing Sheets

METHOD AND DEVICE FOR DETECTING BIOELECTRIC SIGNALS

PRIORITY

This application claims the benefit of DE 10 2015 219 037.4, filed on Oct. 1, 2015, which is hereby incorporated by reference in its entirety.

FIELD

The present embodiments relate to a method for operating a differential measurement arrangement, and to an associated bioelectric differential measurement arrangement for detecting bioelectric signals.

BACKGROUND

During the measurement of bioelectric signals (e.g., ECG signals), common-mode interference signals occur as a result of non-ideal measurement inputs of the measurement arrangement. Common-mode interference signals are interference resulting from common-mode signals such as may arise, for example, from the power supply system frequency at 50 Hz.

Common-mode interference signals occur if dissimilar conditions, such as different impedances and capacitances, occur at the two measurement inputs during a differential signal measurement. One example of a conventional measurement arrangement for measuring an electrocardiogram (ECG) is illustrated in FIG. 1.

Figure 1:
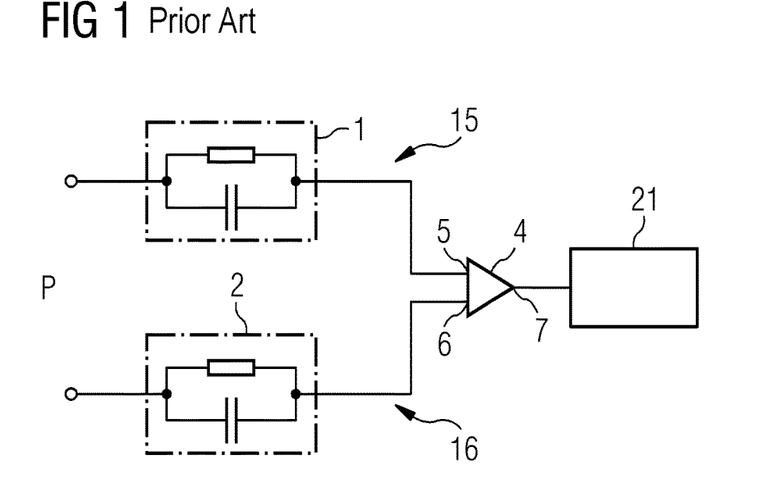
FIG. 1 shows a block diagram of an ECG measurement arrangement in accordance with the prior art.

FIG. 1 shows a circuit arrangement for measuring ECG signals of a patient P in accordance with the prior art. The circuit arrangement includes a first electrode 1 and a second electrode 2, which are in contact with the patient P in such a way that a heart current may flow via the electrodes 1 and 2 to a differential amplifier 4. The differential amplifier 4 includes a first input 5, a second input 6, and an output 7. The first input 5 is electrically connected to the first electrode 1, and the second input 6 is electrically connected to the second electrode 2.

The output signal of the amplifier 4 is communicated to a first signal detection unit 12 that detects the signal amplified by the amplifier 4. The two electrodes 1 and 2 are symbolized by an RC element illustrating the impedance values of the two measurement paths 15, 16. In this case, a first measurement path 15 runs from the contact of the first electrode 1 with the patient P via the first electrode 1 to the first input 5 of the amplifier 4, and the second measurement path 16 runs from the contact of the second electrode 2 with the patient P via the second electrode 2 to the second input 6 of the amplifier 4.

Figure 2:
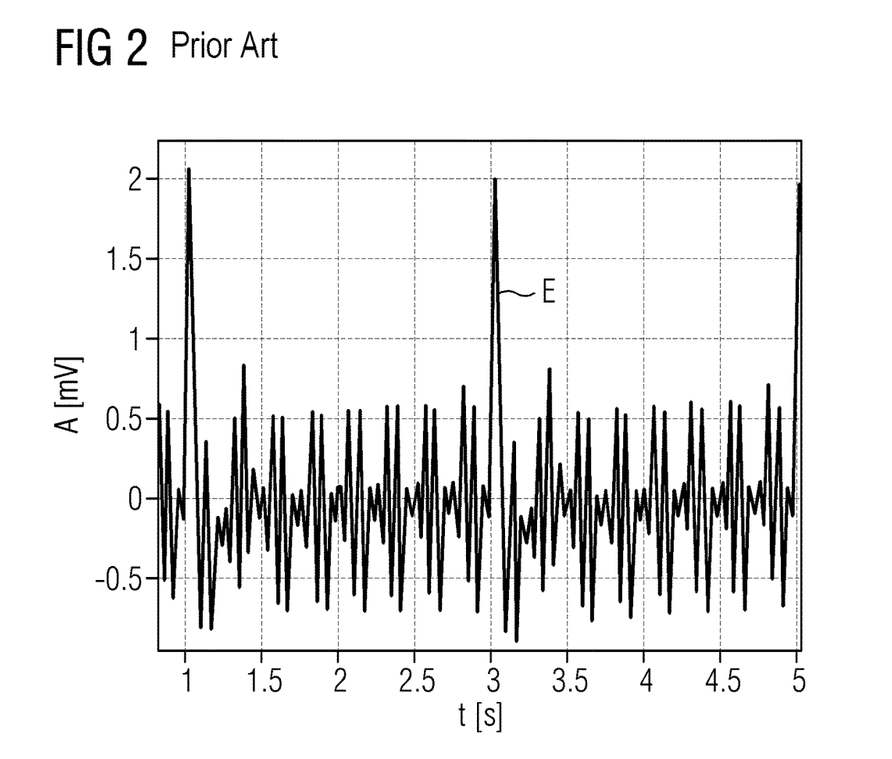
FIG. 2 shows a graph of an ECG signal with a superimposed interference signal in accordance with the prior art.

One example of an ECG signal E subjected to common-mode interference as a result of an impedance difference of 500 kohms is shown in FIG. 2. The associated measurement set-up corresponds to the set-up in FIG. 1. In the graph shown, the amplitude A of the ECG signal E in mV is plotted against time t in seconds. The amplitude A of the interference sources is approximately 1.3 mV in the example with an impedance difference of 500 kohms. In this example, there is a strong ECG signal E having an amplitude A of more than 2 mV, but there are also patients P having an amplitude A of only 0.1 mV, which would completely vanish in these interference sources. In the case of larger impedance differences, the amplitude A of the common-mode interference signals rises further and may also reach a multiple of the representation shown.

In principle, common-mode signals (e.g., interference signals) are not concomitantly amplified in a differential measurement arrangement, and so the common-mode signals are suppressed. However, the different impedances of the inputs of the measurement arrangement have the effect that different input signals caused by the same interference signal are present at the two inputs of an amplifier circuit of a differential measurement arrangement, such that the then differential interference signal is amplified together with the actual measurement signal. These common-mode interference signals are very strong in the application on the patient (e.g., a human being or an animal), since the electrode contacts on the patient's skin have a greatly varying quality factor without complex preparation.

An electrode contact on the patient may have impedances of between 10 kohms and several megohms and likewise greatly varying capacitances. As a result, the difference between the impedances and capacitances at two measurement inputs is also in the range of up to several megohms. One example of an ECG signal E subjected to common-mode interference by such an impedance difference of 500 kohms is shown in FIG. 2. In some instances, the impedance differences at the inputs of the measurement arrangement are even higher, such that an evaluation of a measurement signal is hardly possible or may lead to incorrect diagnoses.

By contrast, the total sum of the impedances of the electrode contacts is hardly of importance on account of progress in circuit technology with input impedances of from hundreds of megohms to several gigaohms; it is completely irrelevant to the common-mode interference signals.

A method for suppressing common-mode interference during the measurement of bioelectric signals is not permissible in all cases of diagnosis since the latter in part normatively requires a guaranteed transfer function of the represented measurement data, but that may not be guaranteed by adaptive methods. However, common-mode interference signals are interfering in a diagnostic environment and may lead to incorrect diagnoses.

Hitherto the assessment of signal interference in a diagnostic environment has been incumbent on the physician, who, on the basis of the measurement signal composed of useful signal and interference signal, is to determine himself/herself which signal components are diagnostically significant and which are caused by interference.

In order to minimize the proportion of interference, the medical personnel ought therefore to provide a good and stable electrode-skin contact resistance and thus as far as possible symmetrical measurement paths. However, even with very good contact resistances, freedom from interference is not guaranteed since a perfect symmetry is not possible just on account of tolerances in the measurement set-up. Only few measurement devices carry out an impedance measurement of the electrode contact resistance in order to provide the medical personnel with assistance when attaching the electrodes.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method and a device that support a diagnostic evaluation of bioelectric signals are provided.

A method for operating a bioelectric differential measurement arrangement, where, besides the useful signal interfered by common-mode signals, the interference signal is also determined by the differential measurement arrangement is provided. Both signals unchanged or changed or indicators derived therefrom are offered to an operator of the differential measurement arrangement.

A method for operating a bioelectric differential measurement arrangement includes detecting a bioelectric measurement signal. The measurement signal includes a bioelectric useful signal and an interference signal. The method also includes simultaneously detecting the interference signal using a common-mode current measurement by the same bioelectric differential measurement arrangement. Both signals unchanged or changed are presented to a user.

For a diagnostic evaluation, the precise signal profile of the measurement signals, which is often unusual owing to physiological dictates, is relevant. In the case of differential measurements, the signal profile, as described above, may be influenced by external interference, which in some instances, is hardly discernible as such or not discernible as such at all. The measurement and representation of the causative interference signal or of an indicator regarding the extent to which an interference signal maps onto the useful signal may facilitate the evaluation of the measurement signals for clinical personnel. The risk of incorrect diagnoses is reduced as a result.

In one development of the method, the bioelectric measurement signal and the interference signal are simultaneously represented over time.

In a further embodiment, the bioelectric measurement signal and the impedance-scaled interference signal are represented over time, where the previously determined impedances of electrodes of the measurement arrangement are used for scaling the interference signal. As a result, the interference becomes representable in terms of absolute magnitude in a manner appropriate for the measurement signal.

In a further embodiment, the bioelectric measurement signal and the impedance-scaled interference signal may be represented differently in color in a common graph. By way of example, the measurement signal is colored black, and the interference signal is colored red.

In one development of the method, an interference indicator is determined from the interference signal. The interference indicator represents a measure of the degree of interference of the bioelectric measurement signal, and the bioelectric measurement signal and the interference indicator are optically represented over time.

In a further embodiment, a correlation indicator that represents a measure of the correlation between the bioelectric measurement signal and the interference signal is determined, and the bioelectric measurement signal and the correlation indicator are optically represented over time.

In a further embodiment, a bioelectric measurement signal freed of an interference signal is determined, and the bioelectric measurement signal freed of an interference signal is additionally optically represented over time.

In one configuration, an analysis of the interference signal may be carried out. The analysis determines the type of physical processes causing the interference.

In one development, the analysis may be based on a feature comparison in the time and/or frequency domain and performs a comparison with stored interference patterns.

Using the classification of interference, the patient environment may be improved in a targeted manner by the clinical user, such that less or no interference arises and each measurement becomes qualitatively better even with poor electrode contact resistances. On account of the interference sources that are otherwise very difficult to analyze, this is an advantage in dealing with common-mode interference and for assessing improvements of these interference sources. As a second aspect, the classification in the case of the application of ECG measurements in the vicinity of large appliances may be used by the manufacturer of the large appliances to detect the interference emissions of the large appliances and to minimize the interference emissions in a targeted manner.

A measurement arrangement for measuring and representing bioelectric measurement signals includes a differential voltage measurement system that detects the bioelectric measurement signal and the interference signal by the method according to one or more of the present embodiments.

In one development, the measurement arrangement includes a display unit that represents the determined signals or indicators.

In a further embodiment, the differential voltage measurement system includes the following components: a first electrode and a second electrode that are connected to a patient at the input and make available a respective measurement contact at the output; a shunt resistor connected in series with the second electrode; a first amplifier circuit having a first input for a first signal from the first electrode and a second input for a second signal from the second electrode and an output; a second amplifier circuit having a first input and a second input, where the first input of the second amplifier circuit is connected between the shunt resistor and the second input of the first amplifier circuit and the second input of the second amplifier circuit is connected between the second electrode and the shunt resistor, and an output; a first signal detection unit at the output of the first amplifier circuit; and a second signal detection unit at the output of the second amplifier circuit, which detects the signal from the second amplifier circuit as a measurement variable of the current intensity of a common-mode current.

DETAILED DESCRIPTION

The present embodiments are described in detail below based on the example of an ECG measurement and ECG signals (as a bioelectric measurement signal). The present embodiments are analogously applicable in further bioelectric measurements (e.g., in an EEG measurement).

Figure 3:
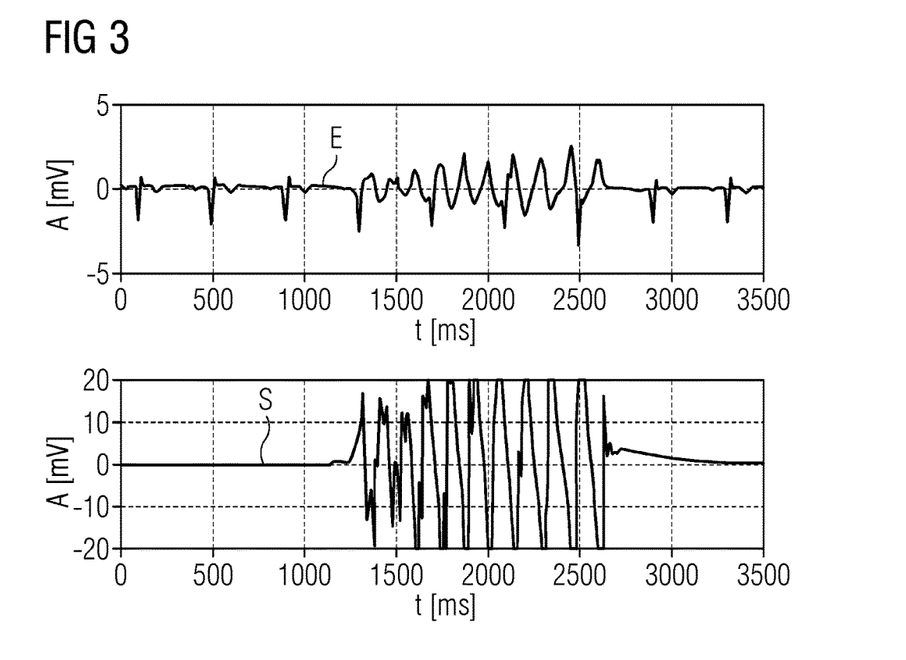
FIG. 3 shows a graph of an ECG signal and a graph of an interference signal.
Figure 7:
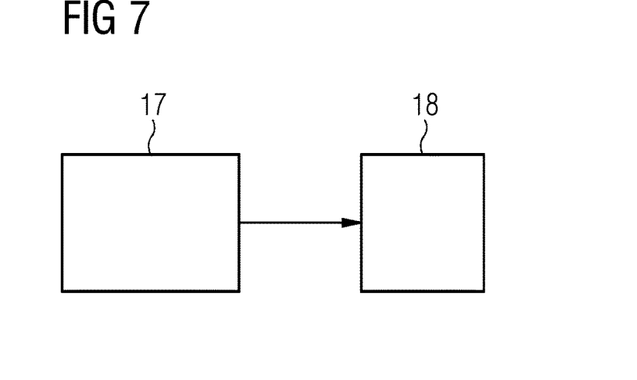
FIG. 7 shows a block diagram of a bioelectric measurement arrangement.
Figure 8:
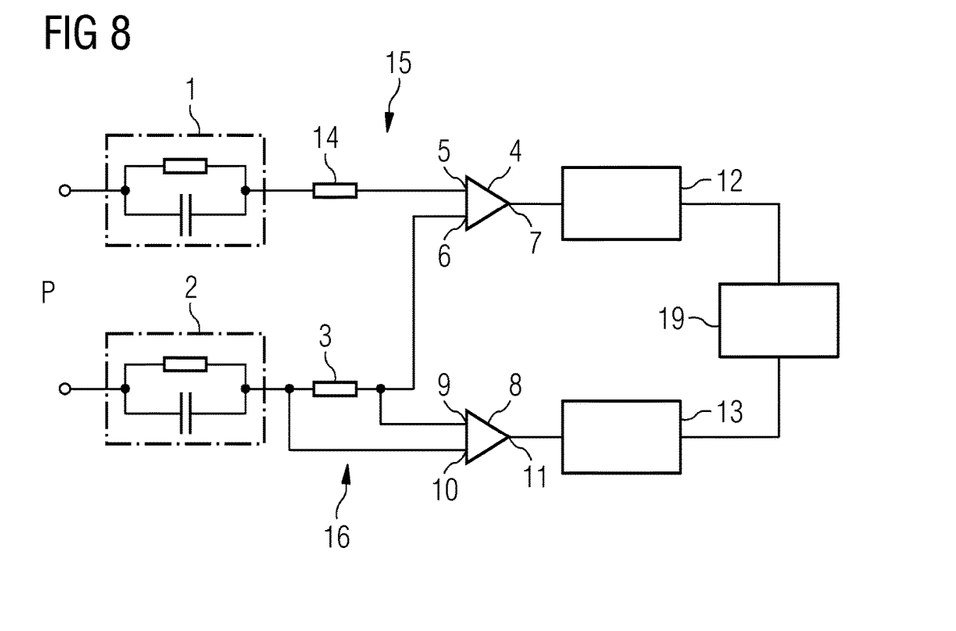
FIG. 8 shows a block diagram of a differential voltage measurement system.

FIG. 3 shows a graph of an ECG signal E and a graph of an interference signal S, where amplitudes A in mV are plotted against time t in ms. The interference signal S and the ECG signal E were measured simultaneously by a differential measurement arrangement, where the interference signal S is determined from a current measurement of a common-mode signal. FIG. 7 and FIG. 8 show such a measurement arrangement by way of example.

In the ECG signal E, interference in the range of 1300 ms to 2750 ms is clearly discernible, which is caused by the interference signal S. The recording and/or representation of the common-mode current measurement as a further measurement signal make(s) it easier for the medical personnel to separate useful signal and interference. Based on this extended measurement data, it is easier to assess that the signal section indicating ventricular fibrillation in the ECG between 1250 ms and 2750 ms is very probably attributable to a common-mode signal interference.

Figure 4:
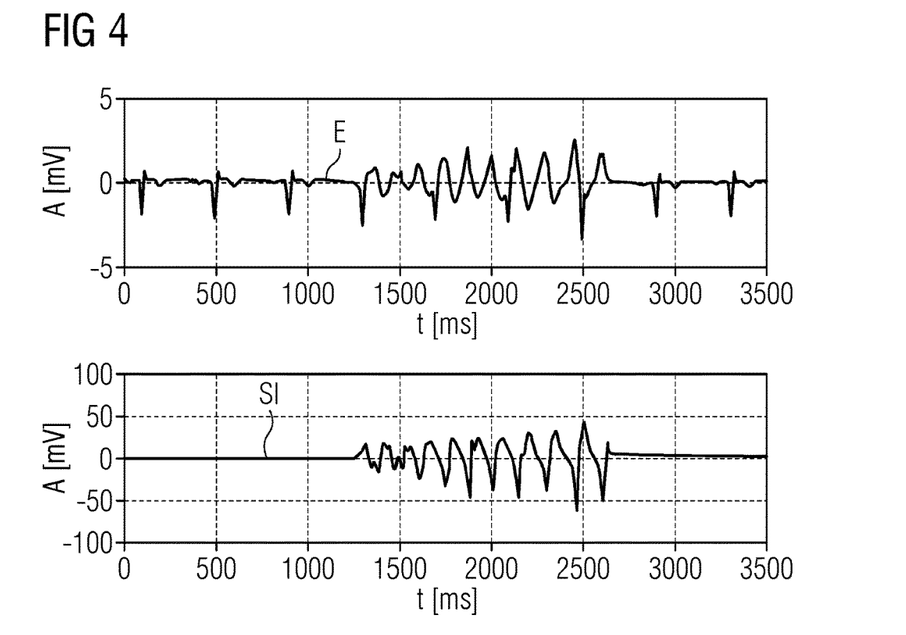
FIG. 4 shows a graph of an ECG signal and a graph of an impedance-scaled interference signal.

FIG. 4 shows a graph of an ECG signal E and a graph of an impedance-scaled interference signal SI, where the amplitudes A in mV are plotted against time t in ms. The interference signal SI and the ECG signal E were measured simultaneously by a differential measurement arrangement, where the interference signal SI is determined from a current measurement of a common-mode signal. FIG. 7 and FIG. 8 show an associated measurement arrangement by way of example.

Using an independently performed measurement of the impedance of the electrodes, the interference signal SI may be represented in a scaled manner such as may be predicted as a result of these impedances and the measured interference signal on the differential useful signal. The interference in the range of between 1250 ms and 2750 ms is once again discernible.

Figure 5:
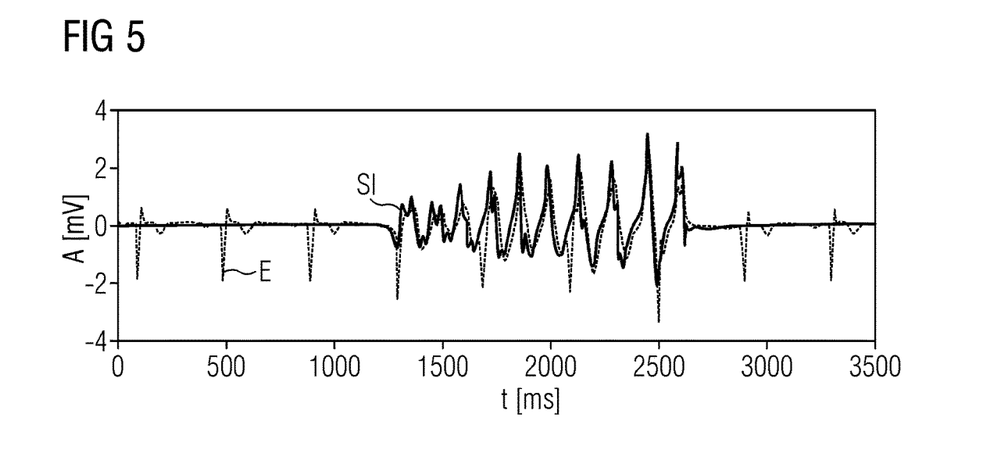
FIG. 5 shows a graph of an ECG signal and of an impedance-scaled interference signal.

FIG. 5 shows a graph of an ECG signal E and an impedance-scaled interference signal SI, where the amplitudes A in mV are plotted against time t in ms. The interference signal SI and the ECG signal E were measured simultaneously by a differential measurement arrangement, where the interference signal SI is determined from a current measurement of a common-mode signal. FIG. 7 and FIG. 8 show such a measurement arrangement by way of example.

The two signal profiles E and SI are plotted in a single graph and represented with different line thicknesses for the purpose of better distinguishability. The interference in the range of 1250 ms and 2750 ms is once again clearly discernible. Alternatively, the signal profiles E and SI may also be represented in different colors or different distinguishing features in a graphic.

The superimposition of the signal profiles E and SI in a single graph illustrates the relationship between the impedance-scaled interference signal SI and the ECG signal E more clearly.

Figure 6:
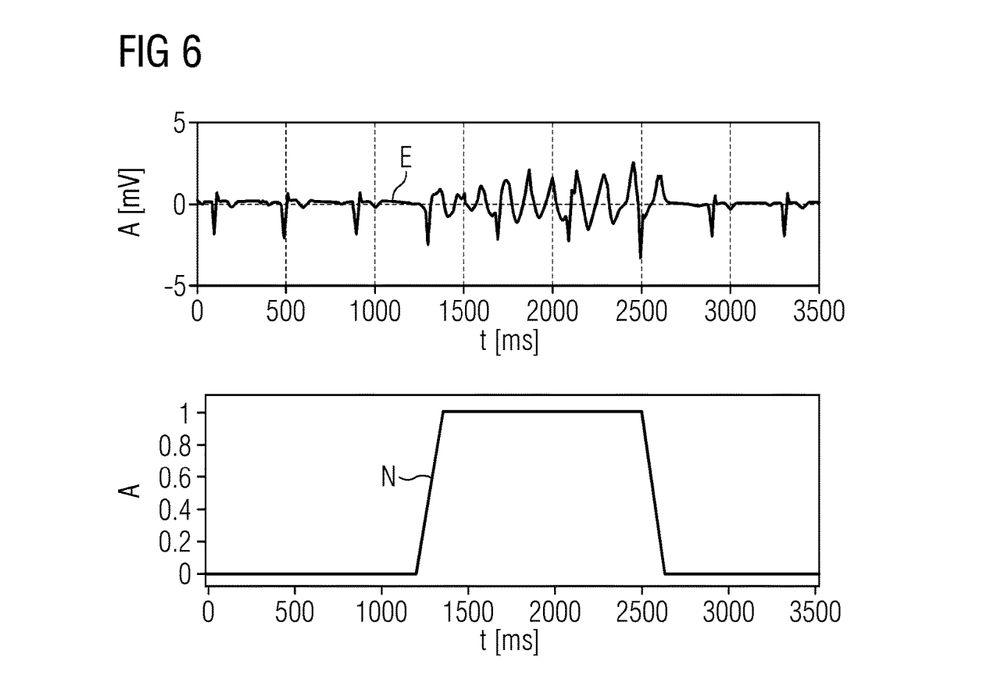
FIG. 6 shows a graph of an ECG signal and a graph of an interference indicator.

FIG. 6 shows a graph of an ECG signal E and a graph of an interference indicator N, where the amplitude A of the ECG signal E in mV and that of the interference indicator N dimensionless are plotted against time t in ms.

Instead of representing the measured, possibly impedance-scaled, interference signal S or SI, a simplified interference indicator N is calculated from the interference signal S and, for example, the measured impedances of the electrodes. The interference indicator represents a measure of the expected degree of interference of the ECG signal E. The interference indicator N may be represented for clinical personnel not only as a graph but, for example, also as a numerical value or in a simplified visualization similar to traffic lights.

In FIG. 6, the interference indicator N is represented as a graph with the values zero to one, where the interference indicator N is increased during the interference phase between 1250 ms and 2750 ms and is otherwise zero.

In a manner similar to the interference indicator N, but based on the measured useful and interference signals, a correlation indicator reflecting the degree of correspondence between useful signal and interference signal may be calculated, and, like the interference indicator N, the correlation indicator may be represented in a wide variety of forms for medical personnel.

Continuously or upon attainment of a specific interference or correlation indicator, in the case of an interactive user interface, an estimation of the useful signal may be displayed to the user in addition to the other displays. Based on this first display, the medical personnel may decide which signal will continue to be displayed, the measured ECG signal or the signal estimated to be free of interference.

An analysis of the interference signal S makes it possible to deduce what type of physical processes causes the interference. The analysis of the interference signal S may be carried out by a classifier, for example, which in the time or frequency domain searches for predefinable features and compares the predefinable features with stored interference patterns. Frequent physical processes are, for example, the movement of isolated, statically chargeable parts and the friction thereof. By way of example, a heart-lung pump maintaining a specific frequency provides for a very periodic interference pattern. Other frequent instances of interference in everyday clinical practice originate from injection pumps or movements of the patient or the clinical personnel if they wear clothing including plastic portions. The identified types of causes of interference are represented for the user following the classification, such that the user may improve the surroundings of the user such that interference is avoided.

From the measured interference signal S, the amplitude of the interference on the useful signal may also be estimated (e.g., with knowledge of the electrode-skin contact resistances). In the case of a very small interference signal S, the interference on the useful signal would be small even with very poor electrodes, whereas in the case of a very large interference signal S, the interference would still be large even with well bonded electrodes.

Based on the impedance measurement and the estimation of the expected interference on the useful signal, the user is then given the recommendation of attaching the electrodes anew and better or, alternatively, changing the work environment, such as, for example, going to a different room with the patient if no improvement may be achieved by attaching the electrodes anew.

Compared with a simple impedance measurement and a recommendation derived therefrom for reattaching electrodes, the addition of the interference information fulfills two points: a) A poor impedance is disadvantageous only if relevant interference occurs simultaneously; and b) even when there is good impedance, the useful signal may be disturbed by very strong interference. An attempted better application of the electrodes is then pointless.

As a result, electrodes are to be reapplied only if it is actually expedient and thus significantly less frequently than owing to a pure impedance measurement. Consequently, the method entails a saving of time and costs for the clinical personnel and a gain in quality as a result of warning in the case of very strong interference that may not be improved even by reapplication of electrodes.

In the further context, the quality of the measurements is thus also increased since the experience that undisturbed measurements are possible even with poor electrodes may lead the clinical personnel legitimately to doubt and permanently ignore the meaningfulness of the impedance measurement.

FIG. 7 shows a block diagram of a bioelectric measurement arrangement including a differential voltage measurement system 17 and a display unit 18 connected thereto. The voltage measurement system 17 measures both the bioelectric measurement signal, such as an ECG signal E, for example, and the interference signal S. On the display unit 18, the curve profiles of the two signals and, if appropriate, other parameters, as described with regard to FIG. 3 to FIG. 6, are represented and offered to the medical personnel for examination and assessment of the diagnostic relevance.

FIG. 8 illustrates a circuit arrangement for a differential measurement of ECG signals in accordance with the subsequently published patent application DE 10 2014 219 943.3 in the name of the same applicant. A first electrode 1 is connected by an input to a patient P. The first electrode 1 is part of a first measurement path 14 including the first electrode 1 and additionally a resistor 15. A second electrode 2 is likewise electrically connected by an input to the patient P. The second electrode 2 is connected by an output to a shunt resistor 3 and with the shunt resistor 3 forms a second measurement path 16.

A first amplifier circuit 4 includes a first input 5 and a second input 6 and an output 7. The first amplifier circuit 4 is connected by the first input 5 to the first electrode 1 via the resistor 14. The first amplifier circuit 4 is electrically connected by the second input 6 via the shunt resistor 3 to the second electrode 2. The output 7 of the first amplifier circuit 4 is connected to an input of a first signal detection unit 12. An output of the first signal detection unit 12 is connected to an input of an evaluation unit 19.

A second amplifier circuit 8 includes a first input 9 and a second input 10, where the first input 9 of the second amplifier circuit 8 is connected between the shunt resistor 3 and the second input 6 of the first amplifier circuit 4, and the second input 10 of the second amplifier circuit 8 is connected between the second electrode 2 and the shunt resistor 3. The second amplifier circuit 8 is electrically connected by an output 11 to a second signal detection unit 13.

The first amplifier circuit 4 serves for detecting the bioelectric measurement signals (e.g., the heart currents of the patient P). It forwards to the first signal detection unit 21 a signal corresponding to the difference between the signals detected by the first electrode 1 and the second electrode 2. The signal possibly still has common-mode components, however.

The second amplifier circuit 8 serves to determine a voltage drop at the shunt resistor 3 that is proportional to the common-mode current flowing in the second measurement path 16, and to forward the determined voltage drop to the second signal detection unit 13.

The evaluation unit 19 may include an adaptive filter, for example, that is set in a manner dependent on the signal detected by the second signal detection unit 13 and filters the signal detected by the first signal detection unit 12 such that the common-mode component of the measurement signal detected by the first signal detection unit 12 is suppressed.

Alternatively, an arrangement constructed analogously to the measurement circuit in FIG. 4 may have a multi-channel set-up. A multiplex circuit may also be provided in the case of a multi-channel measurement arrangement. The circuit is fashioned significantly more compactly for the same number of measurement paths.

Figure 9:
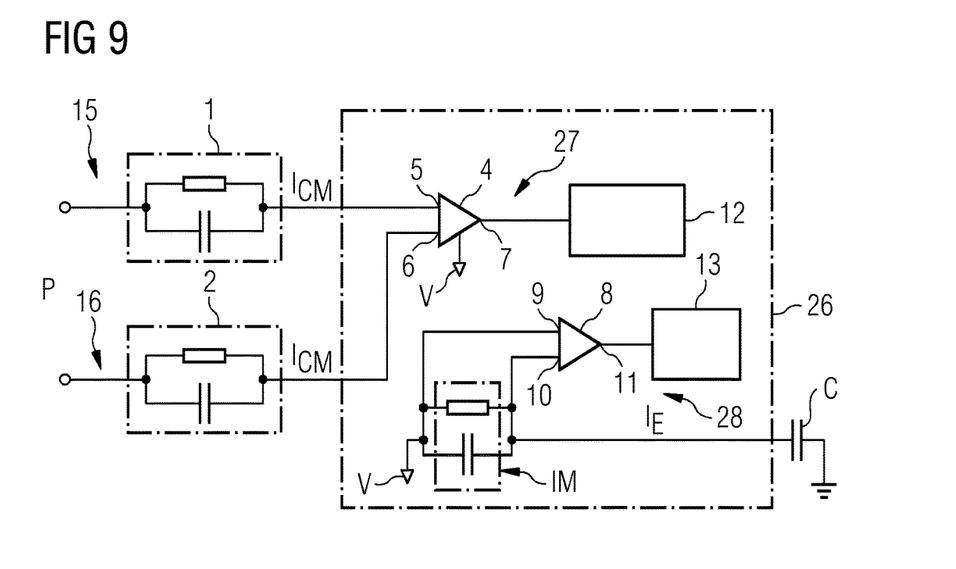
FIG. 9 shows another differential voltage measurement system.

FIG. 9 schematically illustrates a further differential voltage measurement system (e.g., an ECG measurement circuit). The differential voltage measurement system includes two measurement paths 15, 16 and a signal measurement component 26 (e.g., an ECG component) including two measurement circuits 27, 28. The first measurement circuit 27 is, for example, a signal measurement circuit that measures, for example, an ECG signal beset by a common-mode current. The second measurement circuit 28 (referred to hereinafter as interference signal measurement circuit) serves for measuring the interfering common-mode currents and is configured to measure common-mode currents by measuring a current on a path from a potential V of the ECG component 26 via a parasitic capacitance or a protective capacitor configured for ESD protection, illustrated as impedance IM in FIG. 9, to ground.

The signal measurement circuit 27 (e.g., ECG measurement circuit) includes a first electrode 1, which is connected by an input to a patient P. The first electrode 1 is part of the first measurement path 15 including the first electrode 1. The signal measurement circuit 27 includes a second electrode 2, which is likewise electrically connected by an input to the patient P. In this case, the second electrode 2 is part of the second measurement path 16.

The signal measurement circuit 27 includes a first amplifier circuit 4 having a first input 5 and a second input 6 and an output 7. The first amplifier circuit 4 is connected by the first input 5 to the first electrode 1 and is electrically connected by the second input 6 to the second electrode 2. The output 7 of the first amplifier circuit 4 is connected to an input of a first signal detection unit 12.

The second measurement circuit (e.g., the interference signal measurement circuit 28) for measuring the interfering common-mode currents is illustrated at the bottom right in FIG. 9. The interference measurement circuit 28 is not connected directly to the ECG measurement circuit 27, but rather only via a reference potential V, which is also referred to as the potential V of the ECG component. The potential V may be, for example, the potential of the housing of the voltage measurement system of the ECG component.

As shown in FIG. 9, in the interference signal measurement circuit 28, a current $I_E$ flows from the reference potential V via an impedance IM and via an additional capacitance C to ground. The impedance IM serves for converting the current flowing to ground into an electrical voltage that is measurable by the interference signal measurement circuit 28. The additional capacitance C may include, for example, a parasitic capacitance, a capacitor, or an ESD protective capacitor.

The interference signal measurement circuit 28 includes a second amplifier circuit 8 having a first input 9, a second input 10, and an output 11. The first input 9 of the second amplifier circuit 8 is electrically connected to that end of the impedance IM that is at the reference potential V, and the second input 10 of the interference signal measurement circuit 28 is electrically connected to that end of the impedance IM that is arranged on the ground side. The output of the interference signal measurement circuit 28 is electrically connected to a second signal detection unit 13. If a current $I_E$ then flows from the potential V of the ECG component in the direction of ground, the current may be measured with the aid of the interference signal measurement circuit 28.

Advantageously, the current $I_E$ flowing via the additional current path has an intensity several orders of magnitude greater than the current $I_{CM}$ through the first and second measurement paths 15 and 16. Moreover, a measurement in the additional current path also has no influence on the input circuitry. Such a circuit also functions with the use of a right leg drive (e.g., driver circuit for the right leg), also referred to as an RLD path. In this case, the current $I_E$ flowing to ground may have a value one to three orders of magnitude higher than the current flowing through the measurement paths 15, 16. As already mentioned, in the case of the signal measurement circuit shown in FIG. 8, although the measurement path for the measurement of the common-mode currents or common-mode signals is not actually directly in the signal measurement circuit, it is still in the region of influence of the analog input circuitry. The circuit arrangement according to FIG. 9, by contrast, shares only the common reference potential and is thus maximally decoupled, which advantageously leads to a minimization, if not total elimination, of the interference of the ECG measurement paths by the measurement of the common-mode currents.

Figure 10:
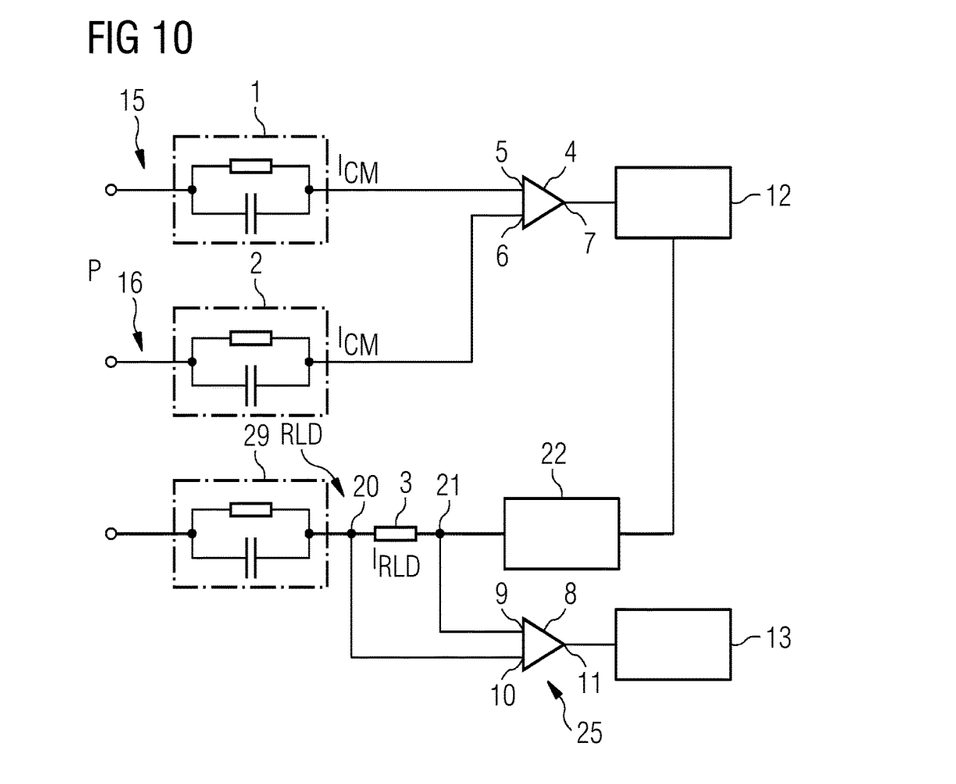
FIG. 10 shows yet another differential voltage measurement system.

FIG. 10 schematically illustrates a further differential voltage measurement system (e.g., an ECG measurement circuit), in which the common-mode current is measured in a separate current path designed as an RLD path. In such a current path, a current $I_{RLD}$ that is approximately one to three orders of magnitude greater than the currents $I_{CM}$ through the first measurement path 15 and through the second measurement path 16 of the measurement circuit flows. In a manner similar to the measurement circuit shown in FIG. 9, the measurement circuit shown in FIG. 10 includes a first measurement path 15 having a first electrode 1, which is connected by an input to a patient P, and a second measurement path 16 having a second electrode 2, which is likewise electrically connected by an input to the patient P.

The measurement circuit shown in FIG. 10 also includes a first amplifier circuit 4 including a first input 5 and a second input 6 and an output 7. The first amplifier circuit 4 is electrically connected by the first input 5 to the first electrode 1 and electrically connected by the second input 6 to the second electrode 2. The output 7 of the amplifier circuit 4 is electrically connected to an input of a first signal detection unit 12.

In addition, the first signal detection unit 12 is connected to a driver circuit 22 (also referred to as right leg drive). The driver circuit 22 is connected to the patient P via an additional path RLD with an additional contact 29. Via the additional path, also referred to as RLD path, a reference potential is applied to the patient P. The driver circuit 22 serves for generating a signal that is regulated to the average common-mode voltages of individual or all signals or may be set to a fixed voltage value. In addition, a shunt resistor 3 is arranged between the driver circuit 22 and the contact 29. The voltage dropped across the shunt resistor 3 is determined by a voltage measurement device 25. The voltage measurement device 25 includes a second amplifier circuit 8, that measures a voltage dropped across the shunt resistor 3 and forwards the measured voltage to a second signal detection unit 13. The second amplifier circuit 8 includes a first input 9 and a second input 10 and an output 11. The first input 9 is connected to the end 21 of the shunt resistor 3 facing the driver circuit 22, and the second input 10 is connected to the end 20 of the shunt resistor 3 facing the patient P. The output 11 of the second amplifier circuit 8 is electrically connected to a second signal detection circuit 13. The second amplifier circuit 8 is used to measure the voltage dropped across the shunt resistor 3 and thus the common-mode current as a component of the current $I_{RLD}$ through the RLD path RLD.

The total impedance of the RLD path RLD is hardly influenced by the shunt resistor 3 since the shunt resistor 3 has a relatively small value in comparison with the patient protective resistors and the electrode contact resistance. Typical values for the shunt resistor 3 vary in the range of 10 to 100 kohms. The resistance values of the patient protective resistors are typically in the range of 100 to 500 kohms, and values of the electrode contact resistances are usually in the range of 10 kohms 2 Mohms.

Although the invention has been more specifically illustrated and described in detail by the exemplary embodiments, the invention is not restricted by the examples disclosed. Other variations may be derived therefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a bioelectric differential measurement arrangement, the method comprising:
    detecting a bioelectric measurement signal, wherein the bioelectric measurement signal comprises a bioelectric useful signal and an interference signal;
    detecting the interference signal using a common-mode current measurement by the bioelectric differential measurement arrangement; and
    representing the bioelectric measurement signal and the interference signal, a changed interference signal, or an interference indicator determined from the interference signal on a display unit.

2. The method of claim 1, further comprising:
    optically representing the bioelectric measurement signal over time; and
    optically representing the interference signal over time.

3. The method of claim 1, further comprising:
    optically representing the bioelectric measurement signal over time; and
    optically representing an impedance-scaled interference signal over time,
    wherein previously determined impedances of electrodes of the bioelectric differential measurement arrangement are used for scaling the interference signal.

4. The method of claim 3, wherein the bioelectric measurement signal and the impedance-scaled interference signal are represented differently in color in a common graph.

5. The method of claim 1, further comprising:
determining an interference indicator from the interference signal, the interference indicator representing a measure of a degree of interference of the bioelectric measurement signal;
optically representing the bioelectric measurement signal over time; and
optically representing the interference indicator over time.

6. The method of claim 1, further comprising:
determining a correlation indicator, the correlation indicator representing a measure of a correlation between the bioelectric measurement signal and the interference signal;
optically representing the bioelectric measurement signal over time; and
optically representing the correlation indicator over time.

7. The method of claim 1, further comprising:
determining a bioelectric measurement signal freed of an interference signal; and
optically representing the bioelectric measurement signal freed of an interference signal over time.

8. The method of claim 1, further comprising:
analyzing the interference signal, the analyzing comprising determining a type of physical processes causing the interference.

9. The method of claim 8, wherein the analyzing is based on a feature comparison in a time domain, a frequency domain, or the time domain and the frequency domain and carries out a comparison with stored interference patterns.

* * * * *